(12) United States Patent
Li et al.

(10) Patent No.: US 9,157,112 B2
(45) Date of Patent: Oct. 13, 2015

(54) SPECIFIC DOUBLE-STRANDED PROBES FOR HOMOGENEOUS DETECTION OF NUCLEIC ACID AND THEIR APPLICATION METHODS

(75) Inventors: Qingge Li, Xiamen (CN); Jixuan Liang, Xiamen (CN); Guoyan Luan, Xiamen (CN)

(73) Assignee: Quandx, Inc., Menlo Park, CA (US)

( * ) Notice: Subject to any disclaimer, the term of this patent is extended or adjusted under 35 U.S.C. 154(b) by 320 days.

(21) Appl. No.: 12/854,619

(22) Filed: Aug. 11, 2010

(65) Prior Publication Data

US 2011/0129828 A1 Jun. 2, 2011

Related U.S. Application Data

(62) Division of application No. 10/398,832, filed as application No. PCT/US01/31246 on Oct. 5, 2001, now Pat. No. 7,799,522.

(30) Foreign Application Priority Data

Oct. 10, 2000 (CN) .................................. 00 1 30711
Jan. 13, 2001 (CN) .................................. 01 1 01446

(51) Int. Cl.
*C12Q 1/68* (2006.01)
*C07H 21/00* (2006.01)
*C07H 21/04* (2006.01)

(52) U.S. Cl.
CPC .............. *C12Q 1/6813* (2013.01); *C07H 21/00* (2013.01); *C07H 21/04* (2013.01); *C12Q 1/6818* (2013.01); *C12Q 1/6844* (2013.01)

(58) Field of Classification Search
None
See application file for complete search history.

(56) References Cited

U.S. PATENT DOCUMENTS

| | | | |
|---|---|---|---|
| 4,766,062 A | 8/1988 | Diamond et al. | |
| 5,716,784 A | 2/1998 | Di Cesare | |
| 5,925,517 A | 7/1999 | Tyagi et al. | |
| 6,150,097 A | 11/2000 | Tyagi et al. | |
| 6,361,942 B1 * | 3/2002 | Coull et al. | ................ 435/6.11 |
| 6,365,729 B1 | 4/2002 | Tyagi et al. | |
| 6,593,091 B2 | 7/2003 | Keys et al. | |

(Continued)

FOREIGN PATENT DOCUMENTS

| | | |
|---|---|---|
| AU | 57754/86 | 11/1986 |
| EP | 0070685 | 1/1983 |

(Continued)

OTHER PUBLICATIONS

Morrison et al., Homogeneous Detection of Specific DNA Sequences by Fluorescence Quenching and Energy Transfer, Journal of Fluorescence, vol. 9, No. 3, 1999, pp. 187-196.*

(Continued)

*Primary Examiner* — Samuel Woolwine
(74) *Attorney, Agent, or Firm* — Fox Rothschild LLP; Gerard P. Norton; Jianming J. Hao

(57) ABSTRACT

Nucleic acid detection probes that comprise a pair of complementary, fluorophore/quencher labeled oligonucleotides, one of which is shorter than the other, are able to detect single-stranded and double-stranded targets in hybridization reactions and amplification reactions with real-time detection. Double-stranded probes of equal length are useful in PCR amplification reactions with real-time detection.

20 Claims, 5 Drawing Sheets

(56) References Cited

U.S. PATENT DOCUMENTS

| | | | |
|---|---|---|---|
| 7,799,522 | B2 | 9/2010 | Li et al. |
| 7,803,528 | B1 * | 9/2010 | Chiang et al. ............... 435/6.11 |

FOREIGN PATENT DOCUMENTS

| | | | |
|---|---|---|---|
| EP | 0070685 | A2 | 1/1983 |
| EP | 0229943 | | 12/1986 |
| EP | 0229943 | A2 | 7/1987 |
| EP | 0232967 | | 8/1987 |
| EP | 0232967 | A2 | 8/1987 |
| EP | 0601889 | | 12/1993 |
| EP | 0601889 | A2 | 6/1994 |
| WO | 95/13399 | A1 | 5/1995 |
| WO | 9513399 | | 5/1995 |
| WO | 96/34983 | A1 | 11/1996 |
| WO | 9634983 | | 11/1996 |
| WO | 97/32044 | A1 | 9/1997 |
| WO | 9732044 | | 9/1997 |
| WO | WO 97 32044 | * | 9/1997 ............... C12Q 1/68 |
| WO | 97/39008 | A1 | 10/1997 |
| WO | 9739008 | | 10/1997 |
| WO | 00/14278 | A1 | 3/2000 |
| WO | 0014278 | | 3/2000 |

OTHER PUBLICATIONS

Landegren et al., Reading Bits of Genetic Information: Methods for Single-Nucleotide Polymorphism Analysis, Genome Res. 1998 8: pp. 769-776.*
Gotoh et al., A New Approach to Determine the Effect of Mismatches on Kinetic Parameters in DNA Hybridization Using an Optical Biosensor,DNA Research 2, 285-293 (1995).*
Wetmur, DNA Probes: Applications of the Principles of Nucleic Acid Hybridization,Critical Reviews in Biochemistry and Molecular Biology, 26(3/4):227-259 ( 199 1 ).*
Marras et al. Multiplex detection of single-nucleotide variations using molecular beacons. Genetic Analysis: Biomolecular Engineering 14:151-156 (1999).*
GenBank EU370621 [online] Aug. 23, 2010 [retrieved on Feb. 22, 2015] retrieved from http://www.ncbi.nlm.gov/nuccore/eu370621.*
Applied Biosystems Reagents and Consumables Sequence Detection Systems [online] [retrieved on Feb. 22, 2015] retrieved from https://pmgf.osu.edu/sites/pmgf.osu.edu/files/Consumables-ApplBio.pdf.*
Guo et al. Enhanced discrimination of single nucleotide polymorphisms by artificial mismatch hybridization. Nature Biotechnology 15:331-335 (1997).*
Santa Lucia (1998) Proc. Natl. Acad. Sci. USA vol. 95: pp. 1460-1465.
Hyndman et al. (1996) Biotechniques vol. 20 No. 6; pp. 1090-4, 1096-7.
Office Action mailed Jul. 25, 2006 in counterpart JP Application 2002-534331 (and English translation).
Morrison et al., "Solution-Phase Detection of Polynucleotides Using Interacting Fluorescent Labels and Competitive Hybridization" Analytical Biochemistry (1989) 183, 231-244.
Holland et al., "Detection of specific polymerase chain reaction product by utilizing the 5'-3' exonuclease activity of *Thermus aquaticus* DNA polymerase" Proc. Natl. Acad. Sci. USA (1991) vol. 88, pp. 7276-7280.
Biswas, et al., "Branch Migration Through DNA Sequence Heterology," J. Mol. Biol., (1998) 279, 795-806.
Ellwood, et al., "Strand Displacement Applied to Assays with Nucleic Acid Probes" Clinical Chemistry (1986) 32/9, 1631-1632.
Harrison et al., "Screening for oligonucleotide binding affinity by a convenient fluorescence compeition assay" Nucleic Acids Research (1999), vol. 27, No. 17 e14.
Li et al., "A new class of homogeneous nucleic acid probes based on specific displacement hybridization" Nucleic Acids Research (2002) vol. 30, No. 2 e5.
Reynaldo, et al., "The Kinetics of Oligonucleotide Replacements" J. Mol. Biol. (2000) 279, 511-520.
Tyagi et al., "Molecular Beacons: Probes that Fluoresce upon Hybridization" Nature Biotechnology, (1996) 14, pp. 303-308.
Vary, C.P.H., "A Homogeneous nucleic acid hybridization assay based on strand displacement" Nucleic Acids Research (1987) vol. 15, pp. 6883-6897.
Vary, et al., "Nonisotopic Detection Methods for Strand Displacement Assay of Nucleic Acids" Clinical Chemistry (1986) vol. 32, No. 9, 1696-1701.
Office Action issued on Mar. 3, 2010 for U.S. Appl. No. 10/398,832.
Office Action issued on Jul. 31, 2009 for U.S. Appl. No. 10/398,832.
Office Action issued on Dec. 19, 2008 for U.S. Appl. No. 10/398,832.
Office Action issued on May 12, 2008 for U.S. Appl. No. 10/398,832.
Office Action issued on Jun. 4, 2007 for U.S. Appl. No. 10/398,832.
Office Action issued on Sep. 13, 2006 for U.S. Appl. No. 10/398,832.
Morrison et al (1989) Analytical Biochemistry 183: 231-244.
New England biolab catalog 1993/1994 p. 12-13.
Holland et al. (1991) Proc. Natl. Acad. Sci. USA vil. 88, 99 7276-7280.
SantaLucia (1998) Proc. Natl. Acad. Sci. USA vol. 95: pp. 1460-1465.
Hyndman et al. (1996) Biotechniques vol. 20 No. 6; pp. 1090-1094, 1096-1097.
Biswas, et al., "Branch Migration Through DNA Sequence Heterology" J. Mol. Biol., (1998) 279, 795-806.
Bonnet et al., "Thermodynamic basis of the enhanced specificity of structured DNA probes" Proc. Natl. Acad. Sci. USA (1999) vol. 96, pp. 6171-6176.
Ellwood, et al., "Strand Displacement Applied to Assays with Nucleic Acid Probes" Clinical Chemistry, (1986) 32/9, 1631-1632.
Harrison, et al., "Screening for oligonucleotide binding affinity by a convenient fluorescence competition assay" Nucleic Acids Research, (1999), vol. 27, No. 17, e14.
Holland, et al., "Detection of specific polymerase chain reaction product by utilizing the 5' .fwdarw. 3' exonuclease activity of *Thermus aquaticus* DNA polymerase" Proc. Natl. Acad. Sci. USA (1991) vol. 88, pp. 7276-7280.
Li et al., "A new class of homogeneous nucleic acid probes based on specific displacement hybridization" Nucleic Acids Research, (2002) vol. 30, No. 2 e5.
Morrison, et al., "Solution-Phase Detection of Polynucleotides Using Interacting Fluorescent Labels and Competitive Hybridization" Analytical Biochemistry (1989) 183, 231-244.
Reynaldo, et al., "The Kinetics of Oligonucleotide Replacements" J. Mol. Biol., (2000) 279, 511-520.
Tyagi et al., "Molecular Beacons: Probes that Fluoresce upon Hybridization" Nature Biotechnology, (1996) 14, 303-308.
Vary, C.P.H., "A Homogeneous nucleic acid hybridization assay based on strand displacement" Nucleic Acids Research, (1987) vol. 15, 6883-6897.
Vary, et al., "Nonisotopic Detection Methods for Strand Displacement Assay of Nucleic Acids" Clinical Chemistry, (1986) vol. 32, No. 9, 1696-1701.
Office Action, mailed Jul. 25, 2006, in counterpart JP Application 2002-534331 (and English translation).

* cited by examiner

SEQUENCE LISTING

```
<160> NUMBER OF SEQ ID NOS: 12

<210> SEQ ID NO 1
<211> LENGTH: 22
<212> TYPE: DNA
<213> ORGANISM: Artificial
<220> FEATURE:
<223> OTHER INFORMATION: Probe Strand 1
<220> FEATURE:
<221> NAME/KEY: misc_feature
<223> OTHER INFORMATION: FAM located at 5' end

<400> SEQUENCE: 1
acgaacctca aacagacacc at                                             22

<210> SEQ ID NO 2
<211> LENGTH: 18
<212> TYPE: DNA
<213> ORGANISM: artificial
<220> FEATURE:
<223> OTHER INFORMATION: Probe Strand 2
<220> FEATURE:
<221> NAME/KEY: misc_feature
<223> OTHER INFORMATION: dabcyl located at 3' end

<400> SEQUENCE: 2
tgtctgtttg aggttgct                                                  18

<210> SEQ ID NO 3
<211> LENGTH: 24
<212> TYPE: DNA
<213> ORGANISM: artificial
```

```
<220> FEATURE:
<223> OTHER INFORMATION: Target Strand of Strand Probe 1

<400> SEQUENCE: 3
ccatggtgtc tgtttgaggt tgct                                              24

<210> SEQ ID NO 4
<211> LENGTH: 24
<212> TYPE: DNA
<213> ORGANISM: artificial
<220> FEATURE:
<223> OTHER INFORMATION: Mismatched Target Strand with Single-Nucleotide
      Substitution

<400> SEQUENCE: 4
ccatggtgtc tgtttcaggt tgct                                              24

<210> SEQ ID NO 5
<211> LENGTH: 20
<212> TYPE: DNA
<213> ORGANISM: artificial
<220> FEATURE:
<223> OTHER INFORMATION: Forward Primer for amplification of of the
      human beta-globin gene

<400> SEQUENCE: 5
gaagagccaa ggacaggtac                                                   20

<210> SEQ ID NO 6
<211> LENGTH: 20
<212> TYPE: DNA
<213> ORGANISM: artificial
<220> FEATURE:
<223> OTHER INFORMATION: Reverse Primer for the amplification of of the
      human beta-globin gene

<400> SEQUENCE: 6
caacttcatc cacgttcacc                                                   20

<210> SEQ ID NO 7
<211> LENGTH: 24
<212> TYPE: DNA
<213> ORGANISM: artificial
<220> FEATURE:
<223> OTHER INFORMATION: Positive Probe Strand
<220> FEATURE:
<221> NAME/KEY: misc_feature
<222> LOCATION: (1)..(1)
<223> OTHER INFORMATION: FAM located at 5' end
<220> FEATURE:
<221> NAME/KEY: misc_feature
<222> LOCATION: (26)..(26)
<223> OTHER INFORMATION: Phosphate located at 3' end

<400> SEQUENCE: 7
agcaacctca aacagacacc atgg                                              24

<210> SEQ ID NO 8
<211> LENGTH: 20
<212> TYPE: DNA
<213> ORGANISM: artificial
<220> FEATURE:
<223> OTHER INFORMATION: Negative Probe Strand
<220> FEATURE:
<221> NAME/KEY: misc_feature
<223> OTHER INFORMATION: dabcyl located at 3' end

<400> SEQUENCE: 8
```

```
ggtgtctgtt tgaggttgct                                                    20

<210> SEQ ID NO 9
<211> LENGTH: 24
<212> TYPE: DNA
<213> ORGANISM: artificial
<220> FEATURE:
<223> OTHER INFORMATION: Positive Strand Probe - wild-type sequence of
      human beta-globin
<220> FEATURE:
<221> NAME/KEY: misc_feature
<223> OTHER INFORMATION: FAM located at 5' end
<220> FEATURE:
<221> NAME/KEY: misc_feature
<223> OTHER INFORMATION: Phosphite located at 3' end

<400> SEQUENCE: 9
agcaacctca aacagacacc atgg                                               24

<210> SEQ ID NO 10
<211> LENGTH: 22
<212> TYPE: DNA
<213> ORGANISM: artificial
<220> FEATURE:
<223> OTHER INFORMATION: Negative Strand Probe - wild-type sequence of
      human beta-globin
<220> FEATURE:
<221> NAME/KEY: misc_feature
<223> OTHER INFORMATION: dabcyl located at 3' end

<400> SEQUENCE: 10
atggtgtctg tttgaggttg ct                                                 22

<210> SEQ ID NO 11
<211> LENGTH: 20
<212> TYPE: DNA
<213> ORGANISM: artificial
<220> FEATURE:
<223> OTHER INFORMATION: Primers for beta-globin genes

<400> SEQUENCE: 11
gaagagccaa ggacaggtac                                                    20

<210> SEQ ID NO 12
<211> LENGTH: 20
<212> TYPE: DNA
<213> ORGANISM: artificial
<220> FEATURE:
<223> OTHER INFORMATION: Primer for beta-globin genes

<400> SEQUENCE: 12
caacttcatc cacgttcacc                                                    20
```

SPECIFIC DOUBLE-STRANDED PROBES FOR HOMOGENEOUS DETECTION OF NUCLEIC ACID AND THEIR APPLICATION METHODS

CROSS-REFERENCE TO RELATED APPLICATION

This application is a Divisional of Ser. No. 10/398,832 filed Aug. 12, 2003, which is a 371 National Phase Application of PCT/US2001/31246 filed Oct. 5, 2001. PCT/US2001/31246 claims priority to Chinese Application Nos. 00130711.8 filed Oct. 10, 2000 and 01101446.6 filed Jan. 13, 2001, the disclosures of which are incorporated herein by reference.

This invention relates to novel probes for homogeneous and specific detection, including real-time detection, of nucleic acids.

BACKGROUND OF THE INVENTION

Traditional heterogeneous detection methods for nucleic acid require separation of hybridized and unhybridized probes, while new homogeneous methods eliminate the separation steps, and are more rapid, simple and quantitative. A variety of nucleic acid amplification techniques have been developed and can amplify a specific sequence of nucleic acid to several million copies within 2-3 hours. However, the dominant gel electrophoresis analysis greatly hindered their wide application in clinical diagnostics. Recently, the combination of homogeneous detection with these amplification techniques, especially polymerase chain reaction (PCR), greatly improved nucleic acid based diagnostics. The resulting quantitative real-time PCR assays are becoming increasingly popular.

Current real-time fluorescence PCR assays can be classified into probe format and non-probe format. Probe format assays utilize fluorogenic probes, e.g. 5'-exonuclease (TaqMan™) probes, molecular beacons, fluorescence energy transfer probes, Scorpion probes, light-up probes, etc. Non-probe format assays utilize fluorogenic dyes, e.g. SYBR Green I, to indicate the reaction. The non-probe format, though simple, finds rather limited application due to its inability to discriminate non-specific amplification. In comparison, the probe format with a second recognition step is much more reliable. However, current probes mentioned above are all difficult to design and synthesize, and they are expensive. Another disadvantage of current probes is their limited specificity. Even molecular beacons, which are claimed to be the most specific ones, have to be modified to discriminate single-nucleotide mismatch in some cases.

This invention relates to a new probe that can be a homogeneous and specific probe for nucleic acid detection. This probe is based on a concept different from the current probes. It is simple to design, easy to prepare, inexpensive, extremely specific, and can be combined with any current nucleic acid amplification technique.

Assays with double-stranded probes according to this invention are based on competitive reaction between oligonucleotides rather than direct hybridization as utilized in current probes. This new probe not only can achieve in a much simpler way what the current probes can, but also possesses many advantages over the current probes.

SUMMARY OF THE INVENTION

This invention relates to specially designed probes for nucleic acid detection and their applications. The probes can specifically detect nucleic acid in a homogeneous format. The probes composed two complementary oligonucleotides of differing length that are labeled: one with a fluorophore and the other with quencher or fluorescence acceptor. Under suitable conditions, the probes are double-stranded. When one probe strand hybridizes with target, the fluorophore generates fluorescence change. Certain embodiments can specifically recognize their perfectly matched targets at room temperature, but cannot react with a "target" containing a single-mismatch. Probes according to this invention can be used for real-time nucleic acid amplification detection assays.

Probes according to this invention can comprise DNA, RNA, or mixtures of the two. They can comprise non-natural nucleotides and non-natural nucleotide linkages. Their 3' ends may be blocked to prevent extension. When we refer to "oligonucleotides" of the probes, we mean to include the foregoing.

This invention also relates to assays employing double-stranded probes. Hybridization assays of this invention in which only single-stranded target is present include probes as described above. Assays in which double-stranded target is present, such as typical PCR amplification, can include as well double-stranded probes having complementary oligonucleotides of equal length.

DETAILED DESCRIPTION OF THE INVENTION

Composition of Double-Stranded Probe

Double-stranded probes according to this invention are made of two complementary oligonucleotides of different lengths. One strand is labeled with a fluorophore and the other is labeled with a quencher. In less preferred embodiments, the fluorescence quencher can be replaced by a fluorescence acceptor of the fluorophore. Double-stranded probes can have different structures under different conditions, and this is reflected by the fluorescence change. When self-hybridized in a stable double-stranded structure, the fluorophore and the quencher, or the fluorescence energy donor and the acceptor, are in close proximity. The fluorophore or the energy donor is quenched by the quencher or the energy acceptor, and the probes are non-fluorescent at the emission wavelength of the fluorophore or energy donor. When under denatured conditions, such as in acid, basic or high temperature solution, the two strands of the probe are separated, and the fluorophore (or energy donor) become fluorescent. In the presence of the target in hybridization solution, the longer strand of the probe can spontaneously bind to the target, the double-stranded probe becomes dissociated, and the fluorophore (or energy donor) become fluorescent.

Spontaneous Reaction Between Double-Stranded Probes with their Targets.

Double-stranded probes having strands of different lengths can spontaneously react with single-stranded oligonucleotides in solution. In this reaction, the short strand in the double-stranded probe is displaced by the target oligonucleotide sequence to form a thermodynamically more stable duplex. The resulting dissociation of double-stranded probe produces an increase in fluorescence. In this reaction, easily designed embodiments of the double-stranded probes have the ability to distinguish perfectly matched targets from single-nucleotide mismatched targets at room temperature. This extremely high specificity lies in the fact that mismatched recognition is unfavored when compared with the self-reaction of the double strands of the probe itself. This is superior to single-stranded probes, because single-stranded probe are thermodynamically unstable, and can be hybridize with another single-stranded polynucleotide even there exists a mismatch. Molecular beacons are more specific than linear probes due to their stable stem-loop structure that can outcompete a less stable mismatched reaction. However, the recognition portion of the molecular beacons, the loop, is still single-stranded, and this leaves room for mismatch hybridization, if the stem is not long enough or the loop sequence is too long. This is reflected by a recent report that molecular beacons cannot directly used for single-nucleotide discrimination when combined with NASBA, a well-known isothermal nucleic acid amplification technique.

Figure 1:
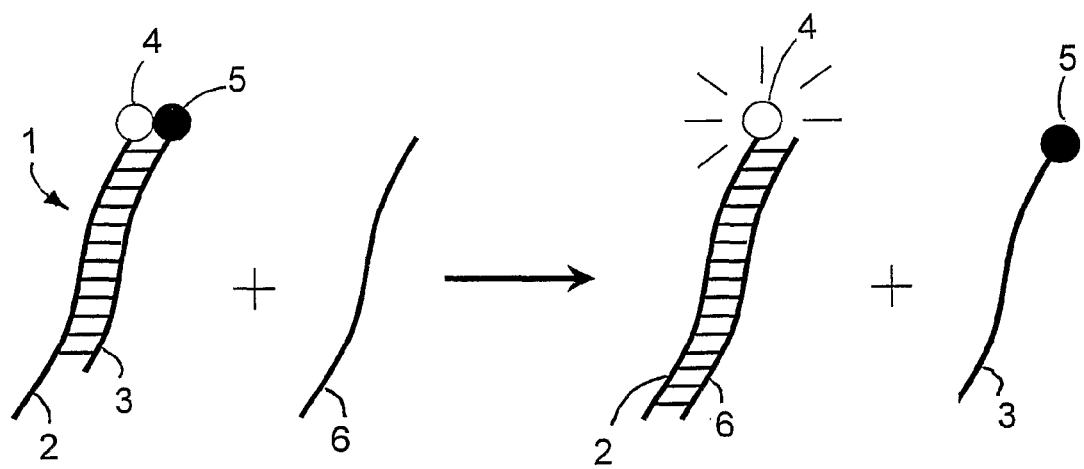
FIG. 1 shows schematic drawing of a double-stranded probe and its working principle.

Referring to FIG. 1, double-stranded probe 1 is composed of two complementary oligonucleotides 2, 3 of different lengths. The longer strand, in this case positive strand 2, is labeled with a fluorophore 4 and the shorter negative strand 3 is labeled with a quencher 5. The probe is non-fluorescent due to the close proximity of the fluorophore and the quencher. In the presence of target 6, negative strand 3 is displaced by the target, and the escaped fluorophore 4 becomes fluorescent. It will be appreciated that fluorescence would also result, if fluorophore 4 and quencher 5 are interchanged.

Combination of Double-Stranded Probes with Nucleic Acid Amplification.

As noted above, double-stranded probes according to this invention can spontaneously react with single-stranded target. We have discovered that they also can be used to detect the newly produced single-stranded amplicon in a real-time format. During a typical PCR cycle comprising high-temperature denaturation, low-temperature annealing and intermediate temperature elongation, double-stranded probes are denatured during the denaturation (or melting) step, and become fluorescent. During the annealing step, in the absence of the target, the two strands of the probe will be in double-stranded conformation, and thus will be are non-fluorescent. In the presence of the target, however, the two probe strands will hybridize with the target. Fluorescence will be produced as a result. During the extension step, the probe strands move off the targets. By measuring the fluorescence during each annealing step of a PCR reaction, amplification can be tracked in a real-time format.

At the annealing stage this probe would undergo self-annealing and become non-fluorescent in the absence of target. However, in the presence of the target, the fluorophore-labeled strand, say the positive strand, of the probe would dissociate from the negative strand, bind to the target, and become fluorescent. When the temperature is increased to allow extension of the primers (72° C.), the two strands of the probe would dissociate from the target and would not interfere with chain extension. By measuring fluorescence intensity during the annealing stage of every cycle, PCR can be followed in a real-time format.

Figure 2:
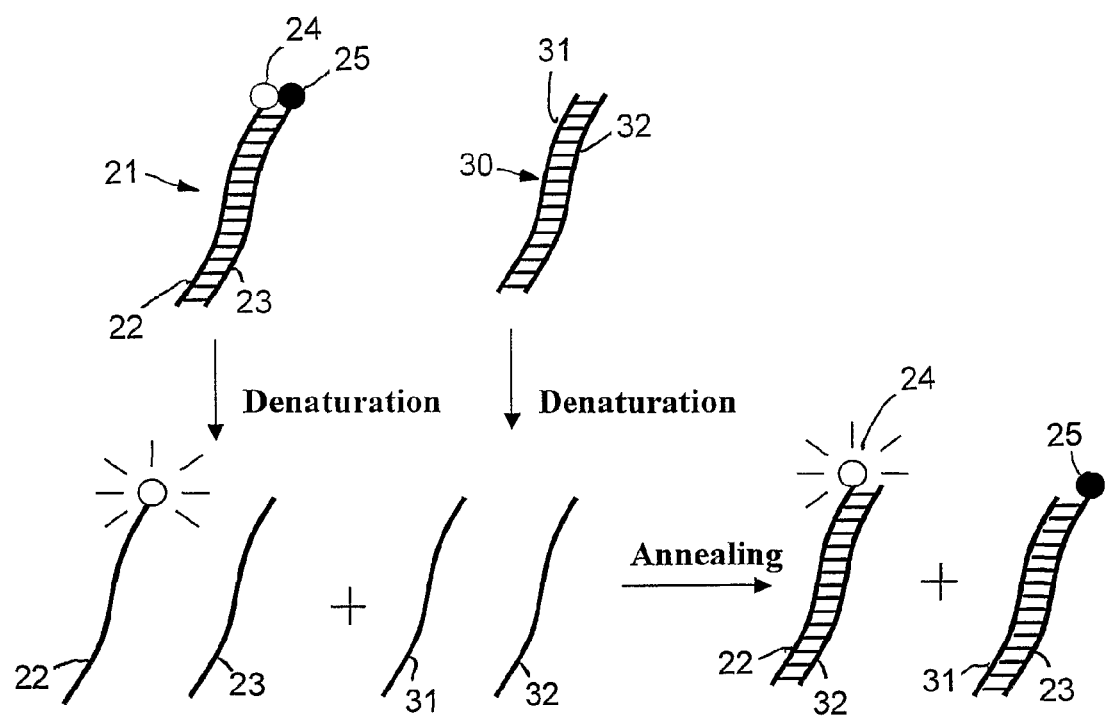
FIG. 2 shows schematic illustration of the working principle of double-stranded probe in PCR detection during denaturation and annealing stages.

Referring to FIG. 2, there is shown a double-stranded probe 21 and a double-stranded amplicon 30, both of which are present in a PCR amplification reaction during an intermediate PCR cycle. Probe 21 comprises strand 22, labeled with fluorophore 24, and complementary strand 23, labeled with quencher 25. The labels are applied to the blunt-end termini of the strands. As depicted, strands 22, 23 are of equal length, which they may be but need not be for use in real-time PCR. Amplicon 30 comprises complementary strands 31, 32. Upon high-temperature denaturation, strands 22, 23 of the probe separate, as do strands 31, 32 of the amplicon. When the temperature is lowered to the annealing temperature (for PCR primer annealing), probe strands 22, 23 anneal, or hybridize, to their complementary target strands 31, 32 of the amplicon. Fluorophore 24 is not quenched by quencher 25, and fluoresces.

Design of Double-Stranded Probes.

The relative length of the two strands: in most cases, the two strands of the probes are different in length, and usually, the longer stand is 1-5 bases longer than the shorter strand for PCR and 2-10, preferably 2-7, bases longer for isothermal allele discrimination. In certain embodiments of assays according to this invention, such as double-stranded probes used in RNA detection or double-stranded probes used in real-time PCR, where both positive and negative target strands compete to hybridize with probe strands, the two strands can be equal in length.

The labeling position of the double-stranded probe: both fluorophore and the quencher can be on the terminal or internal bases. In preferred embodiments, they are on opposed terminal complementary bases of the two strands. In especially preferred embodiments both the fluorophore and the quencher are on the blunt end of the probe. In some cases, especially when the probes are labeled with fluorescence energy transfer donor and acceptor, the position of the labels can be adjusted according the optimal energy transfer. In a preferred but not limiting embodiment, the fluorescence energy donor and acceptor are labeled on the terminal bases of both strands, and one strand is usually blocked with a phosphorate group.

Suitable instrument for double-stranded probes: double-stranded probes can be combined with common nucleic acid amplification, especially PCR, and the amplicon can be measured in both real-time and end-point format. For real-time detection, fluorescence is measured at the annealing temperature. Currently available real-time amplification/detection instruments with which double-stranded probes can be used include the Model 7700 and Model 5700 from Applied Biosystems (ABI), the IQ Cycler from Bio-Rad, the LIGHTCYCLER from Hoffmann-La Roche, and the Rotor-Gene 2000 from Corbett Research, among others.

The Advantages of Double-Stranded Probes

Simple and easy design: there are no additional requirements for the original reaction system when designing double-stranded probes. Probe design itself is much easier compared with current dual-dye-labeled probes or adjacently hybridizing probes. Probes according to this invention can be designed by any persons who are familiar with conventional probe designs.

Cost effective preparation: the labeling procedure involved in preparation of strands for double-stranded probes is only single-dye modification, which can be carried out in any DNA synthesizer without additional technical requirement. Purification involves only one step. This is much superior to other dual-dye-modification of probe strands or internal modification of probe strands, where multiple step modification and purification are needed, and the final yield is greatly reduced, thus increasing expense.

High specificity: it has already been proven by molecular beacons that structure-restricted probes possess higher specificity than conventional linear probes. Double-stranded probes are a kind of structure-restricted probes in this context. The probes can bind to their target only when the free energy produced is greater than that of the double-stranded probe. If there is mutation in the targets, the double-stranded probe may keep its own double-stranded state without any reactions that are thermodynamically not favored.

Example 1

Spontaneous Reaction a of Double-Stranded Probe with its Target

Fifty μL of 0.80 μM double-stranded probe in 10 mM Tris-HCl (pH 8.0) containing 1.5 mM MgCl.sub.2 was maintained at 25° C., and its fluorescence was monitored over time in an Eclipse spectrofluorometer (Varian). Fluorescence intensity was first measured for 2 minutes at 25° C. Then a two-fold molar excess (5 μL of 16 μM solution) of target oligonucleotide was added, and the level of fluorescence was recorded at 15-second intervals. The nucleotide sequences of the two probe strands were 5'-FAM-ACGAACCTCAAACA-GACACCAT-3' (SEQ ID NO 1) (longer strand) and 5'-TGTCTGTTTGAGGTTGCT-dabcyl-3' (SEQ ID NO 2) (shorter strand). The target complementary to the longer strand was 5'-CCATGGTGTCTGTTTGAGGTTGCT-3' (SEQ ID NO 3, and the target containing a single-nucleotide substitution (mismatched target) was 5'-CCATGGTGTCT-GTTTCAGGTTGCT-3' (SEQ ID NO 4), where an underline identifies the nucleotide substitution.

Figure 3:
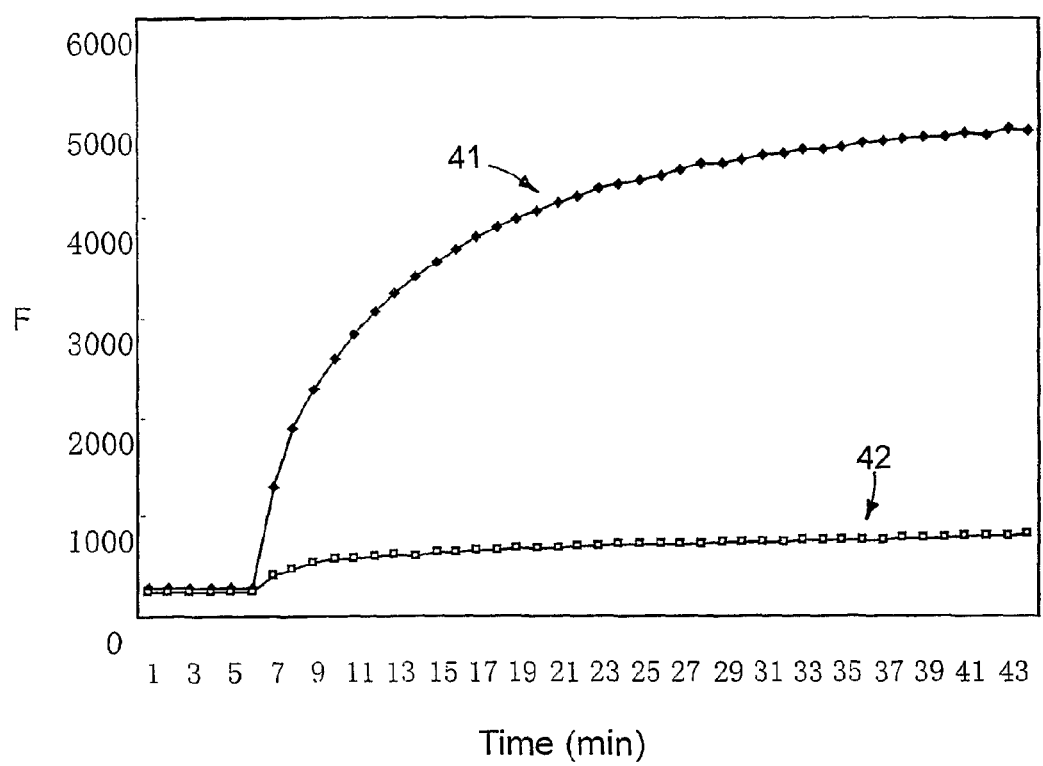
FIG. 3 shows reaction kinetics of double-stranded probe with its perfectly matched and single-nucleotide mismatched target.

FIG. 3 shows the fluorescence (F) observed over time for both the perfectly complementary target (line 41) and for the mismatched target (line 42). It could be observed that over 20 times fluorescence could be achieved. If there is a single-nucleotide mismatch in the target, no fluorescence could be observed.

Example 2

Real-Time PCR Detection of Human 13-Globin with Double-Stranded Probe

To test the utility of double-stranded probes as real-time amplicon detectors in PCR assays, PCR amplifications were performed with a dilation series of target. Each 50 μL reaction contained 5 μL serially diluted template, 0.2 μM double-stranded probe, 0.4 μM of each primer, 2.0 units of Taq polymerase, 200 μM of each deoxyribonucleoside triphosphate, 50 mM KCl, 2.0 mM MgCl$_2$, and 10 mM Tris-HCl (pH 8.3). After denaturation at 94° C. for 5 min, 40 cycles of amplification (95° C. for 30 sec, 50° C. for 30 sec, and 72° C. for 1 min) were carried out in sealed tubes on a fluorometric thermal cycler (Rotor-Gene 2000, Corbett Research). Fluorescence was recorded at the annealing stage. The original extracted human DNA was serially diluted in tenfold steps and used as template. Water was used in place of the template for the control sample. The double-stranded probe contains a nucleic acid sequence complementary to amplicons made from the target. For simplicity we say that the probe is complementary to the target; however, persons familiar with amplification and detection will understand that by "target" we mean in this case both the original single-stranded target and its complement, both of which are copied in exponential PCR amplification. A 268-base pair fragment of the human β-globin gene (GenBank code HuMMB5E, −195~+73) was amplified. The forward and reverse primers were 5'-GAA-GAGCCAAGGACAGGTAC-3' (SEQ ID NO 5) and 5'-CAACTTCATCCACGTTCACC-3' (SEQ ID NO 6), respectively. The target sequence of the probe was located in the middle of the amplicon. The positive and negative probe strands were 5'-FAM-AGCAACCTCAAACAGACAC-CATGG-PO$_4$-3' (SEQ ID NO 7) and 5'-GGTGTCT-GTTTGAGGTTGCT-dabcyl-3' (SEQ ID NO 8).

Figure 4:
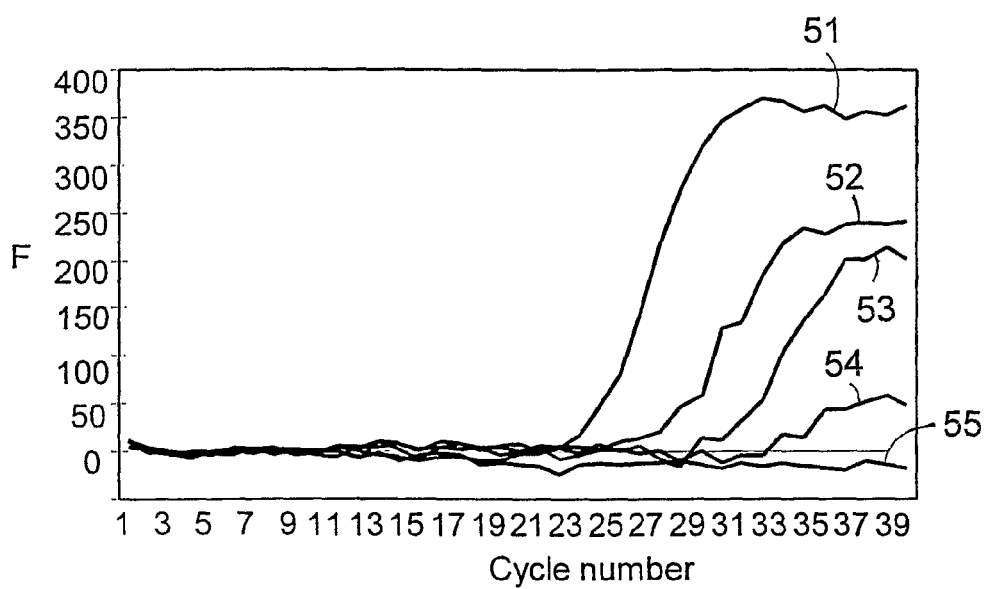
FIG. 4 shows real-time PCR detection with double-stranded probe. From up to down, templates are 10-fold serially diluted until the last one that is water.

The results of real-time detection of fluorescence (F) measured over forty cycles during PCR amplification are shown in FIG. 4. Initial target concentrations in the dilution series decrease from line 51, the most concentrated, to line 54, the least concentrated. Line 55 shows the non-target (water) control.

When present in concentrations similar as the primers, double-stranded probes can react quickly with target strands. The fraction of probes that do not find a target rapidly associate with each other and quench their own fluorescence. Thus, they can be used in real-time nucleic acid amplification assays. In PCR assays for the detection of the human β-globin gene, we chose a negative strand of 20 nucleotides with a melting temperature (Tm) close to that of the primers, and a positive strand of 24 nucleotides in order to obtain a probe-target hybrid that melted about 10° C. higher. We call this probe the "24/20 probe". At the annealing stage this probe undergoes self-annealing and become non-fluorescent in the absence of target. However, in the presence of the target, the positive strand of the probe dissociates from the negative strand, binds to the target, and become fluorescent. When the temperature is increased to allow extension of the primers (72° C.), the two strands of the probe dissociate from the target and do not interfere with chain extension.

Eleven double-stranded probes of different length (22/22 through 22/17 and 20/20 through 20/16) were investigated, and they all worked well in real-time PCR assays, even those in which both strands were the same length. These observations demonstrated the great flexibility in the design of double-stranded probes for real-time PCR.

Example 3

Mutation Detection in Real-Time PCR

To demonstrate the utility of probes according to this invention in single-nucleotide mutation detection with real-time PCR, we prepared two DNA templates (targets) from the human β-globin gene that differed from one another by a single nucleotide substitution. We also prepared a double-stranded probe complementary to the "wild-type" target and a double-stranded probe complementary to the "mutant" target. We designed the probes such that probe-target hybrids would melt about 10° C. higher than a typical PCR annealing temperature (about 50° C.) and about 10° C. lower than the preferred extension temperature (about 72° C.) for Taq DNA polymerase. The probes were 24/20 probes (positive strand 24 nucleotides in length, four nucleotides longer than the negative strand). The probe complementary to wild-type target was labeled with FAM; the probe complementary to mutant target was labeled with Texas Red. Both had dabcyl quenchers. Both were blocked to prevent extension of the probes. Each fluorophore could be distinguishably detected, because the two have different emission spectra. We ran four PCR reactions in which both double-stranded probes were present. The reactions differed as to amplifiable target: none (Negative), wild-type target only (Wild), mutant target only (Mutant), and both wild-type and mutant targets (Wild+Mutant).

Figure 5:
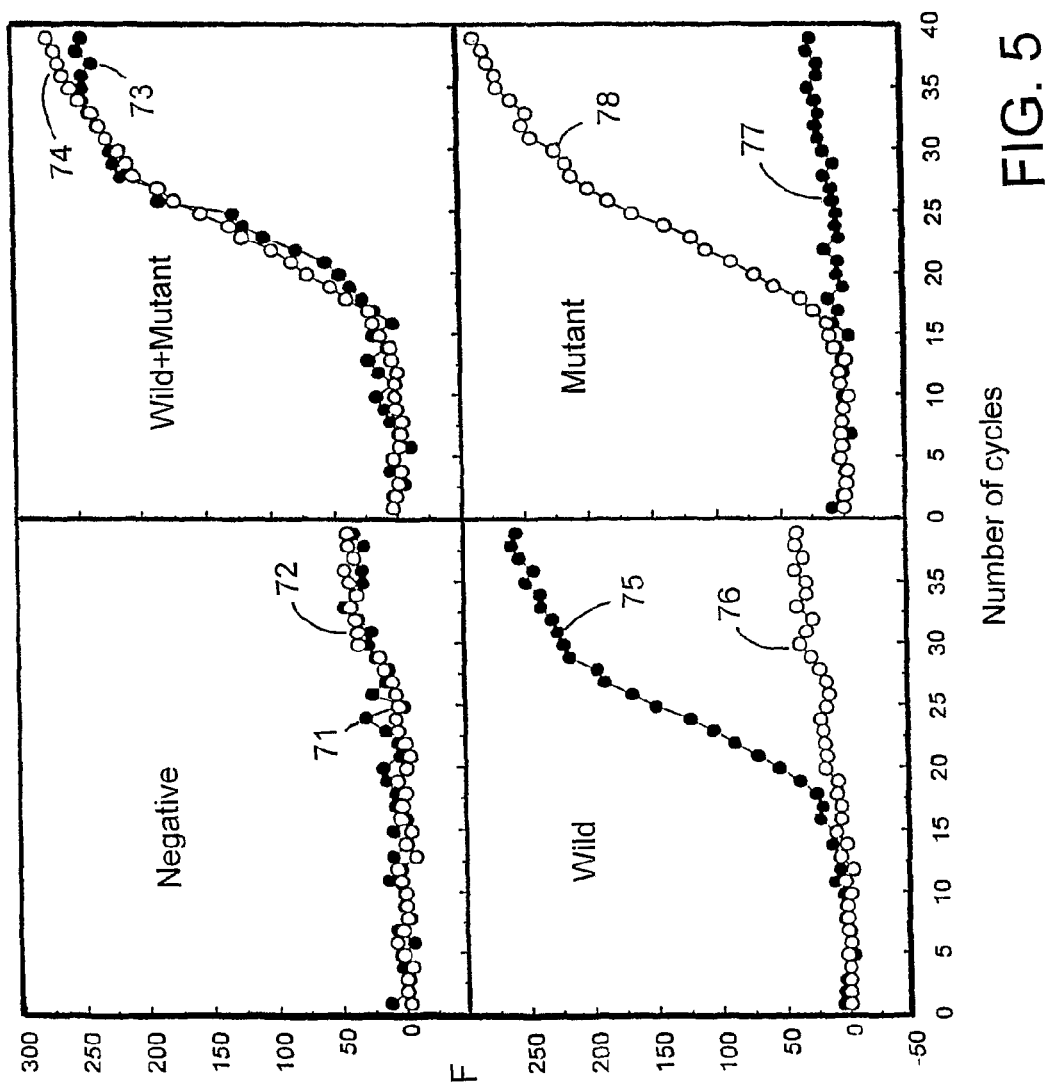
FIG. 5 shows single nucleotide mutation detection with double-stranded probes in real-time PCR utilizing in the same reaction vessel a double-stranded probe complementary to wild-type target and a second double-stranded probe complementary to target with the mutation.

The positive strand of the probe specific to the wild-type sequence of human beta-globin gene was a 24-mer of the sequence: FAM-5'-AGCAACCTCAAACAGACAC-CATGG-3'-$PO_3$ (SEQ ID NO 9) and the negative strand of the probe was a 20-mer of the sequence: 5'-ATGGTGTCT-GTTTGAGGTTGCT-3'-dabcyl. The two strands of the probe specific to the mutant version of beta-globin were: Texas Red-5'-AGCAACCTGAAACAGACACCATGG-3'-PO3 and 5'-ATGGTGTCTGTTTCAGGTTGCT-3'-dabcyl (SEQ ID NO 10). The two strands of each probe were annealed with each other before adding them to the reaction mixture. The DNA templates corresponding to the wild-type and mutant beta-globin genes were prepared by a in vitro mutagenesis method. The primers for the real-time PCR were: 5'-GAA-GAGCCAAGGACAGGTAC-3' (SEQ ID NO 11) and 5'-CAACTTCATCCACGTTCACC-3' (SEQ ID NO 12). Each 50 micro liter reaction contained 5000 copies of templates, 0.4 micro M primers, 0.2 micro M of positive strand and 0.24 micro M of negative strand of each probe, 4.0 mM $MgCl_2$ along with other generic components required for PCR. After incubating the reaction mixtures at 94° C. for 5 min, 40 cycles of the thermal profile 95° C. for 30 sec, 50° C. for 60 sec, and 72° C. for 1 min, were carried out in a fluorometric thermal cycler. The fluorescence was monitored during the annealing steps. The results of real-time fluorescence versus PCR cycle number are shown in FIG. 5. Fluorescence from the probe against wild-type target is shown in filled circles (black dots). Fluorescence from the probe against mutant target is shown in unfilled circles.

With the negative sample, there was no fluorescence (F) either from the wild-type probe, curve 71, or from the mutant probe, curve 72. The result showed that only when template is included in the reaction does one obtain an increase n fluorescence. With both targets present in the sample, fluorescence increased markedly from both the wild-type probe, curve 73, and the mutant probe, curve 74. However, with wild-type target, fluorescence increased markedly from the wild-type probe, curve 75, but not from the mutant probe, curve 76; and, conversely, with mutant target, fluorescence increased markedly from the mutant probe, curve 78, but not from the wild-type probe, curve 77. The results showed that only the matched probe produced the right signal. The discrimination between wild-type template and mutant template was complete, 100%. This proved that probes according to this invention discriminate between targets differing by a single nucleotide. No signals were observed when there were no templates, and two signals were observed when there were two templates.

We have investigated the temperature "window" in which double-stranded probes are able to discriminate single nucleotide mutations. It has been shown in the literature that molecular beacons have a larger window than linear probes and, thus, have better discrimination. Nonetheless, the window for molecular beacons has been shown not to be sufficiently large to permit discrimination at low temperatures, which explains the reported failure of molecular beacons to discriminate such alleles in an isothermal amplification. We have found that double-stranded probes according to this invention have even larger windows, which is believed to make them suitable for discrimination in isothermal amplification reactions.

We claim:

1. A homogeneous amplification and detection method for detecting, in a sample containing a first nucleic acid target sequence, a second target sequence differing from the first target sequence by at least one single nucleotide, comprising the steps of:
   (a) preparing an amplification mixture that includes the sample, primers and other amplification reagents for amplifying said first and second target sequences, and a first quenched, double-stranded hybridization probe having a temperature window in which it is able to discriminate between said second target sequence and a sequence differing therefrom by as little as a single nucleotide, said first probe comprising
      (i) a first oligonucleotide that is labeled with a first fluorophores, that has a 3' end blocked from being extendable by a polymerase, and that consists essentially of a first oligonucleotide sequence that is perfectly complementary to the second target sequence,
      (ii) a quencher-labeled second oligonucleotide that has a 3' end blocked from being extendable by a polymerase and that consists essentially of a second oligonucleotide sequence that is perfectly complementary to said first oligonucleotide sequence but is shorter than said first oligonucleotide sequence by up to seven nucleotides, said labels arranged such that when said first probe is double-stranded, fluorescence from the first fluorophores is quenched;
   (b) subjecting the amplification reaction mixture to an amplification reaction to create copies of the first target nucleic acid sequence and copies of the second target sequence, if the second target sequence is present in the sample;

(c) hybridizing the first oligonucleotide to copies of the second target nucleic acid sequence at a temperature within the temperature window at which the first probe hybridizes to the second target sequence but not to a sequence differing therefrom by as little as a single nucleotide, including said first target sequence; and (d) detecting a fluorescent signal emitted by said first fluorophores upon stimulation, when the first oligonucleotide is so hybridized, said signal indicative of the presence in the sample of the second target sequence but not indicative of the presence in the sample of a sequence differing therefrom by as little as a single nucleotide, including the first target sequence.

2. The method according to claim 1, wherein said first and second oligonucleotides hybridize to produce a double-stranded blunt end, and wherein said fluorophore label and said quencher are attached to said blunt end.

3. The method according to claim 1 wherein at least one of said first and second oligonucleotides comprises at least one non-natural nucleotide or at least one non-natural nucleotide linkage.

4. The method according to claim 1 wherein the amplification reaction is a polymerase chain reaction (PCR) having cycles that include an extension temperature at which the first oligonucleotide dissociates from the second target sequence, the second oligonucleotide sequence is shorter than the first oligonucleotide sequence by 1-5 nucleotides, and detection, whether end-point or real-time, is at a temperature below the extension temperature.

5. The method according to claim 4 wherein the PCR amplification has cycles that include an annealing step at a temperature below the extension temperature, and detection is real-time detection during the annealing step.

6. The method according to claim 4 for detecting a third nucleic acid target sequence that differs from each of said first and second target sequences by at least one nucleotide and that is amplifiable by said primers, wherein the amplification reaction mixture includes a second quenched, double-stranded hybridization probe that discriminates between said third target sequence and each of said first and second target sequences in said temperature window, comprising (iii) a third oligonucleotide that is labeled with a second fluorophore detectably distinguishable from the first fluorophore, that has a 3' end blocked from being extendable by a polymerase and that consists essentially of a third oligonucleotide sequence that is perfectly complementary to the third target sequence, and (iv) a quencher-labeled fourth oligonucleotide having a 3' end blocked from being extendable by a polymerase and consisting essentially of a fourth oligonucleotide sequence that is perfectly complementary to said third oligonucleotide sequence but is shorter than said third oligonucleotide sequence by 1-5 nucleotides, said labels arranged such that when said second probe is double-stranded, fluorescence from the second fluorophore is quenched;

wherein the amplification reaction creates copies of the third target sequence, if the third second target sequence is present in the sample;

wherein hybridizing includes hybridizing the third oligonucleotide to copies of the third target sequence at a temperature at which the second probe is double-stranded in the absence of the third target sequence; and wherein detection includes detecting a fluorescent signal emitted by said second fluorophore when the third oligonucleotide is so hybridized, said signal indicative of the presence in the sample of the third target sequence but not indicative of the presence in the sample of a sequence differing therefrom by at least a single nucleotide, including the first target sequence and the second target sequence.

7. The method according to claim 6, wherein the oligonucleotides of each probe hybridize to produce a double-stranded blunt end, and wherein the fluorophore and quencher labels are attached to said blunt ends.

8. The method according to claim 6 wherein the first, second and third target nucleic acid sequences are alleles amplifiable by a single primer pair.

9. The method according to claim 6 wherein the PCR amplification has cycles that include an annealing step at a temperature below the extension temperature, and detection is real-time detection during the annealing step.

10. The method according to claim 4 wherein the first and second target nucleic acid sequences are alleles amplifiable by a single primer pair.

11. The method according to claim 10 wherein the first and second target sequences differ by a single nucleotide.

12. The method according to claim 1 wherein the second oligonucleotide sequence is shorter than the first sequence by 2-7 nucleotides.

13. The method according to claim 1 wherein the detection is end-point detection.

14. The method according to claim 1 wherein the first and second target nucleic acid sequences are alleles amplifiable by a single primer pair.

15. The method according to claim 14 wherein the first and second target sequences differ by a single nucleotide.

16. The method of claim 1 wherein the amplification reaction mixture includes a second quenched, double-stranded hybridization probe that discriminates between said first target sequence and said second target sequence in said temperature window, said second probe comprising (iii) a third oligonucleotide that is labeled with a second fluorophores detectably distinguishable from the first fluorophores, that has a 3' end blocked from being extendable by a polymerase and that consists essentially of a third oligonucleotide sequence that is perfectly complementary to the first target sequence, and (iv) a quencher-labeled fourth oligonucleotide having a 3' end blocked from being extendable by a polymerase and consisting essentially of a fourth oligonucleotide sequence that is perfectly complementary to said third oligonucleotide sequence but is shorter than said third oligonucleotide sequence by 1-5 nucleotides, said labels arranged such that when said second probe is double-stranded, fluorescence from the second fluorophores is quenched;

wherein hybridizing includes hybridizing the third oligonucleotide to copies of the first target sequence at a temperature at which the second probe is double-stranded in the absence of the first target sequence; and wherein detection includes detecting a fluorescent signal emitted by said second fluorophore when the third oligonucleotide is so hybridized, said signal indicative of the presence in the sample of the first target sequence but not indicative of the presence in the sample of a sequence differing therefrom by as little as a single nucleotide, including the second target sequence.

17. A homogeneous detection method for detecting in a sample containing a first nucleic acid target sequence, at least one additional nucleic acid target sequence differing from said first target sequence by at least one single nucleotide, said additional target sequences differing from one another by at least one single nucleotide, comprising (a) contacting the sample with, for each target sequence to be detected, a quenched double-stranded hybridization probe under conditions in which the probe is double-stranded in the absence of its target sequence, said probe comprising (i) a first oligonucleotide that is labeled with a detectably distinguishable fluorophore, that has a 3' end blocked from being extendable by a polymerase, and that consists essentially of a first oligonucleotide sequence that is perfectly complementary to its target sequence, (ii) a second oligonucleotide that is labeled with a label from the group consisting of a fluorescence quencher and a fluorescence acceptor, that has a 3' end blocked from being extendable by a polymerase, and that consists essentially of a second oligonucleotide sequence that is perfectly complementary to said first oligonucleotide sequence but is shorter than said first oligonucleotide sequence by up to ten nucleotides, said labels of each double-stranded probe being arranged such that when the probe is double-stranded, fluorescence from the fluorophore attached to the first oligonucleotide is quenched, said contacting step being carried out at a temperature within a temperature window at which the first oligonucleotide hybridizes to its target sequence but not to a sequence that differs from said target sequence by as little as a single nucleotide, and (b) stimulating the fluorophore of each first oligonucleotide under said conditions, and detecting fluorescence from each fluorophore, wherein if said sample contains a sequence that is mismatched to a probe's first oligonucleotide sequence by as little as a single nucleotide, that probe's first oligonucleotide does not hybridize thereto and signal.

18. The method of claim 17 wherein the second oligonucleotide of each double-stranded probe is labeled with a quencher.

19. The method of claim 17 wherein said conditions include the annealing temperature of a polymerase chain reaction (PCR) amplification reaction to which the sample has been subjected.

20. A homogeneous amplification and detection method for detecting, in a sample containing a first nucleic acid target sequence, a second target sequence differing from the first target sequence by at least one single nucleotide, comprising the steps of:

(a) preparing an amplification reaction mixture that includes the sample, a pair of primers and other amplification reagents for amplifying said first and second target sequences, and a first quenched, double-stranded hybridization probe comprising (i) a first oligonucleotide that is labeled with a first fluorophore, that has a 3' end blocked from being extendable by a polymerase, and that consists essentially of a first oligonucleotide sequence that is perfectly complementary to the second target sequence, (ii) a quencher-labeled second oligonucleotide that has a 3' end blocked from being extendable by a polymerase and that consists essentially of a second oligonucleotide sequence that is perfectly complementary to said first oligonucleotide sequence but is shorter than said first oligonucleotide sequence by up to seven nucleotides, said labels arranged such that when said first probe is double-stranded, fluorescence from the first fluorophore is quenched;

(b) subjecting the amplification reaction mixture to an amplification reaction to create copies of the first target nucleic acid sequence and copies of the second target sequence, if the second target sequence is present in the sample;

(c) hybridizing the first oligonucleotide to copies of the second target nucleic acid sequence at a temperature at which the free energy released by hybridization of the two oligonucleotides to one another is less than the free energy released by hybridization of the first oligonucleotide to the second target sequence but greater than the free energy released by hybridization of the first oligonucleotide to a sequence differing from the second target sequence by as little as a single nucleotide; and (d) detecting a fluorescent signal emitted by said first fluorophore upon stimulation, said signal indicative of the presence in the sample of the second target sequence but not indicative of the presence in the sample of the first target sequence.

* * * * *